(12) United States Patent
Zaccaria et al.

(10) Patent No.: US 10,888,339 B2
(45) Date of Patent: Jan. 12, 2021

(54) INSTRUMENT FOR ALIGNING FIXING SCREWS TO BE INSERTED IN TRANSVERSE HOLES OF NAILS FOR LONG BONES, IN PARTICULAR MEDULLARY NAILS

(71) Applicant: ORTHOFIX S.R.L., Bussolengo (IT)

(72) Inventors: Andrea Zaccaria, Tregnago (IT); Marco Magni, Ferrara (IT); Daniele Venturini, Povegliano Veronese (IT)

(73) Assignee: ORTHOFIX S.R.L., Bussolengo (IT)

( * ) Notice: Subject to any disclaimer, the term of this patent is extended or adjusted under 35 U.S.C. 154(b) by 18 days.

(21) Appl. No.: 16/302,372

(22) PCT Filed: May 18, 2017

(86) PCT No.: PCT/EP2017/061912
§ 371 (c)(1),
(2) Date: Nov. 16, 2018

(87) PCT Pub. No.: WO2017/198748
PCT Pub. Date: Nov. 23, 2017

(65) Prior Publication Data
US 2019/0216474 A1    Jul. 18, 2019

(30) Foreign Application Priority Data

May 19, 2016    (IT) .................... 102016000051783

(51) Int. Cl.
*A61B 17/90*    (2006.01)
*A61B 17/00*    (2006.01)
(Continued)

(52) U.S. Cl.
CPC ...... *A61B 17/1725* (2013.01); *A61B 17/8615* (2013.01); *A61B 17/888* (2013.01);
(Continued)

(58) Field of Classification Search
CPC . A61B 17/1725; A61B 17/175; A61B 17/171; A61B 17/1717; A61B 17/1721
See application file for complete search history.

(56) References Cited

U.S. PATENT DOCUMENTS 6,039,739 A     3/2000  Simon
6,126,661 A *  10/2000  Faccioli ................ A61B 17/72
                                                       606/64

(Continued)

OTHER PUBLICATIONS

International Preliminary Examining Authority, "Search Report", in application No. PCT/EP2017/061912, dated Apr. 24, 2018, 6 pages.

(Continued)

*Primary Examiner* — Matthew J Lawson
*Assistant Examiner* — Lisa Nguyen
(74) *Attorney, Agent, or Firm* — Hickman Palermo Becker Bingham LLP; Malgorzata A. Kulczcka

(57) ABSTRACT

The invention relates to an improved-structure instrument (1) for allowing the alignment of fixing screws (2) to be inserted in transverse holes (3, 13) of nails (4) for long bones, in particular medullary nails, of the type comprising an arched arm (15) having a free distal end (6) connectable to a proximal end (16) of a head (7) of the nail (4) in which the transverse holes (3, 13) are formed, and a proximal handle portion (5), as well as a connection portion (20) between the distal end (6) and the proximal handle portion (5). Advantageously, the connection portion (2) comprises at least one through-hole (23, 33) for receiving a guide tube (10) for a drilling bit, the through-hole (22, 33) having an axis coinciding with the axis of one of the transverse holes (3, 13) and manually operated quick-locking means (25) are associated with the through-hole (23, 33) so as to lock in a stable position the corresponding tube (10) inserted in the instrument (1).

10 Claims, 9 Drawing Sheets

(51) Int. Cl.
*A61B 17/17* (2006.01)
*A61B 17/88* (2006.01)
*A61B 17/86* (2006.01)

(52) U.S. Cl.
CPC ........ *A61B 17/8883* (2013.01); *A61B 17/862* (2013.01); *A61B 2017/00438* (2013.01); *A61B 2017/90* (2013.01)

(56) References Cited

U.S. PATENT DOCUMENTS

| | | | |
|---|---|---|---|
| 6,702,823 B2 * | 3/2004 | Iaia | A61B 17/1703 606/67 |
| 9,637,937 B2 * | 5/2017 | Wallther | E04G 7/14 |
| 2002/0058949 A1 * | 5/2002 | Iaia | A61B 17/1725 606/98 |
| 2002/0165546 A1 * | 11/2002 | Goble | A61B 17/864 606/310 |
| 2004/0059329 A1 | 3/2004 | Zander | |
| 2005/0281613 A1 * | 12/2005 | Tella | F16D 1/072 403/348 |
| 2008/0264109 A1 * | 10/2008 | Ritchey | A61B 17/8897 66/88 |
| 2014/0052132 A1 * | 2/2014 | Matityahu | A61B 17/748 606/62 |
| 2014/0214101 A1 | 7/2014 | Roethlisberger et al. | |

OTHER PUBLICATIONS

European Patent Office, "Search Report", in application No. PCT/EP2017/061912, dated Dec. 9, 2017, 3 pages.
European Claims in application No. PCT/EP2017/061912, dated Dec. 2017, 3 pages.

* cited by examiner

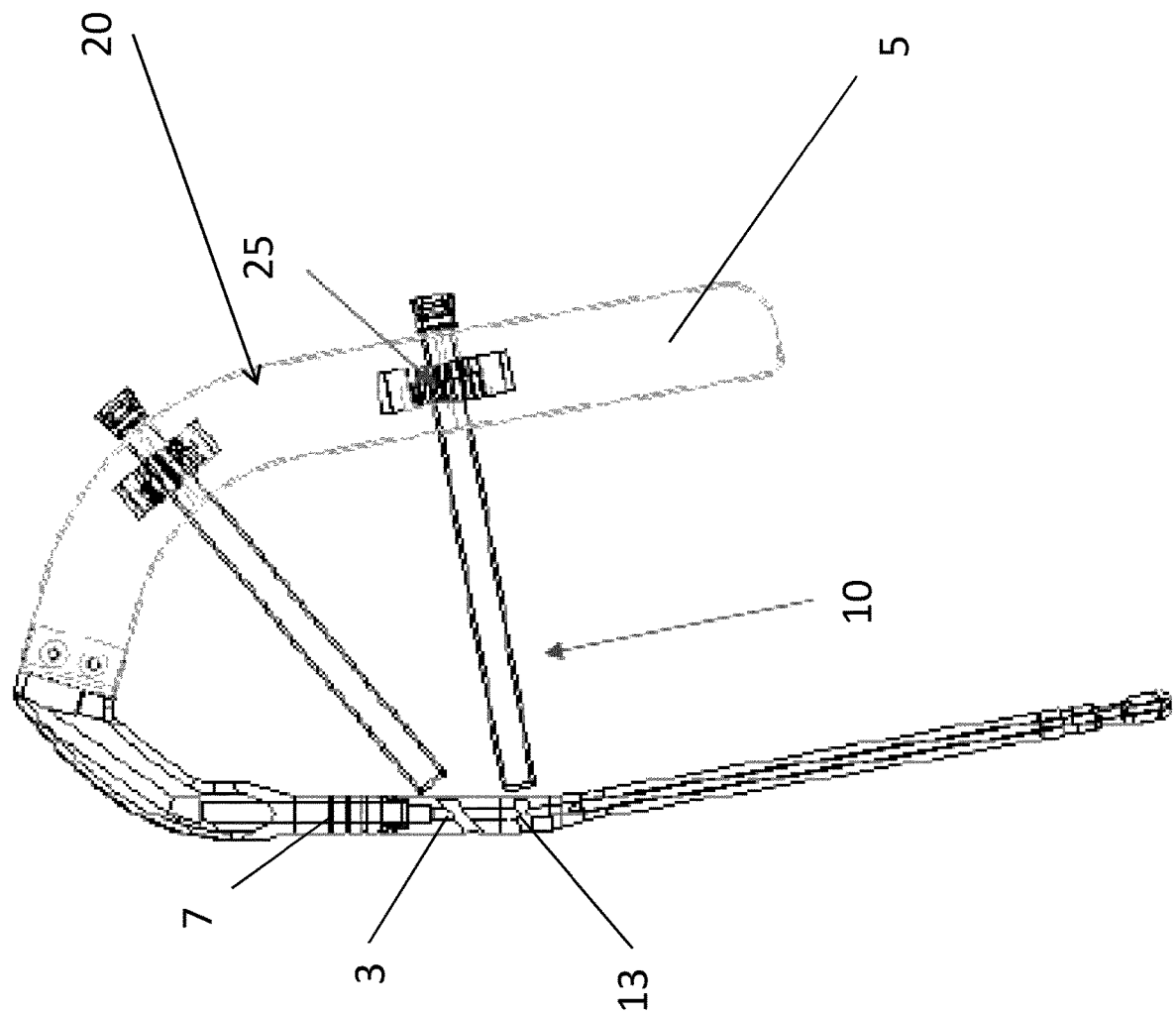

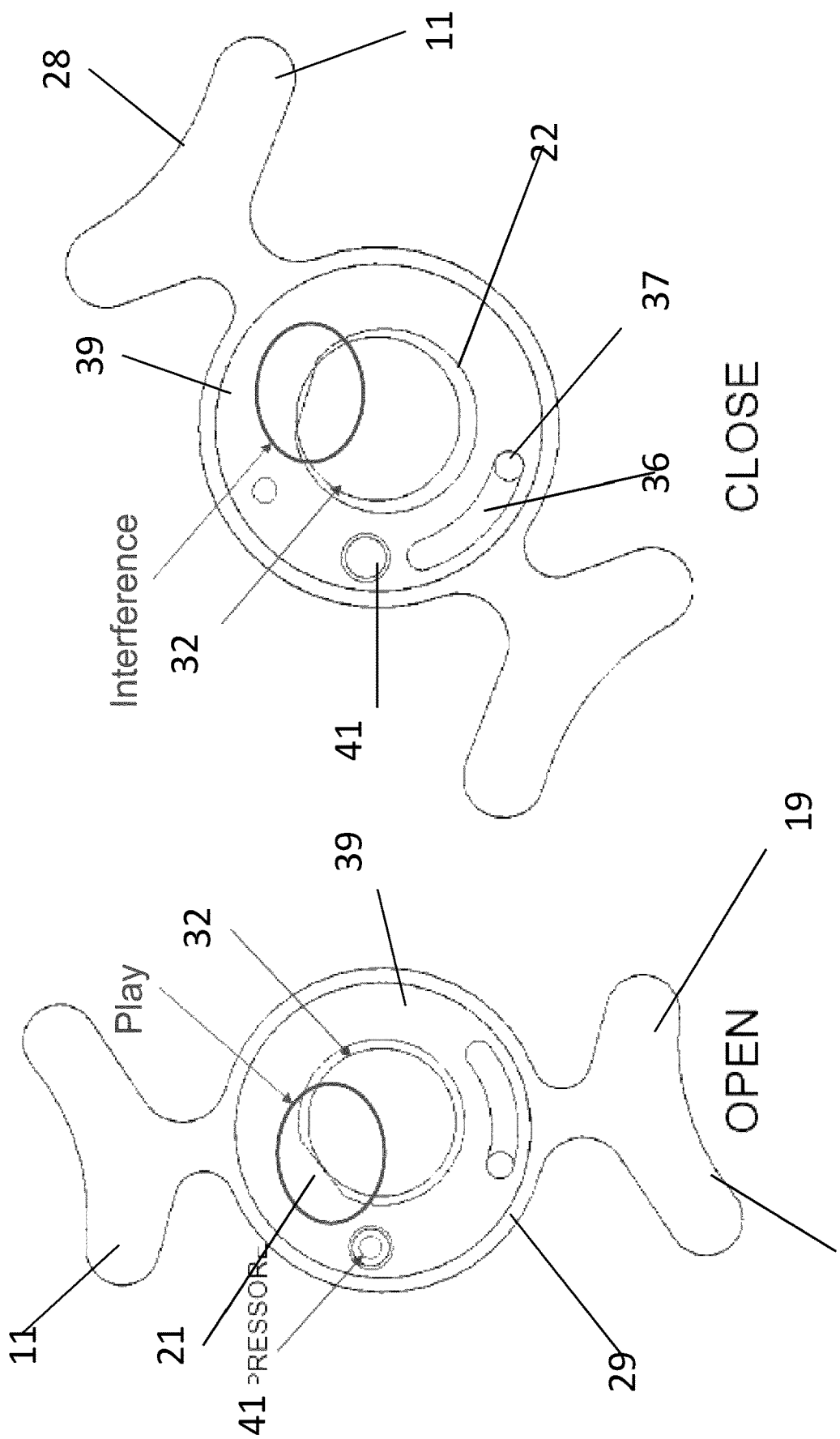

INSTRUMENT FOR ALIGNING FIXING SCREWS TO BE INSERTED IN TRANSVERSE HOLES OF NAILS FOR LONG BONES, IN PARTICULAR MEDULLARY NAILS

The present invention relates to an improved-structure instrument for allowing the alignment of fixing screws to be inserted in transverse holes of nails for long bones, in particular medullary nails.

The invention relates in particular, but not exclusively, to an instrument comprising an arched arm having a free distal end connectable to a proximal end of the nail, and a proximal handle portion, as well as a connection portion between the distal end and the proximal handle portion.

FIELD OF APPLICATION

In the technical sector of the present invention it is known to use long nails which are inserted in the medullary cavity of long bones, such as the femur, the tibia or the humerus, in order to mend fractures which have occurred along a section of the long bone or in the trochanteric portion of a femur.

These nails are provided with transverse through-holes intended to receive bone screws which reach the through-hole penetrating through the cortex of the bone until they reach the medullary nail. The through-holes are not necessarily perpendicular to the main axis of the nail, but may be inclined with respect to this axis depending on their position in the nail or the type of use.

In order to form holes in the bone which may be aligned perfectly with the transverse holes in the medullary nails, usually instruments are used to guide the bone drilling bits so that they are coaxial with the transverse through-holes provided in the medullary nail.

PRIOR ART

An instrument of this type is described for example in U.S. Pat. No. 5,334,192 or in the US patent application No. 2003/220651.

This instrument has an essentially arch-shaped arm with a distal end which is connected to the proximal end of a medullary nail inserted in a long bone, for example a femur, and a proximal handle end provided with through-holes for receiving at least one guide tube.

The through-holes of the handle are oriented so as to be aligned with the transverse holes in the medullary nail, so that a drill bit may be inserted into the hole guide tube so as to perforate under the skin the cortex of the long bone and emerge precisely opposite the inlet of a transverse through-hole.

The handle may be provided with a plurality of through-holes which also have respective axes interfering with each other so as to allow alignment with different transverse through-holes in the medullary nail.

When a guide tube is inserted in one of the aforementioned through-holes of the handle, it must be locked so that it is held stably in position.

Locking in position of the tubes is required by orthopaedic surgeons so as to prevent them from falling in the operating theatre during use and thus becoming no longer sterile.

Moreover, the tubes must be kept axially in a fixed position where the free end is situated adjacent to the bone so as to ensure a precise measurement of the length of the bone screws necessary for the operation, by means of the special instrument.

In some embodiments described for example in the aforementioned patent texts, the handle of the instrument contains a core which is axially slidable and which, upon operation by the user, is able to interfere with the tube portion which passes through the handle so as to fasten it in that position.

However, these embodiments are not particularly convenient and easy to operate manually while the surgical operation is being performed.

In other embodiments a handle is provided with elastically deformable portions which allow the guide tube to be locked in position; however, these solutions have also not proved to be particularly reliable during use.

For instance another known solution is disclosed in the U.S. Pat. No. 6,039,739 disclosing an instrument for allowing the alignment of fixing screws to be inserted in transverse holes of nails for long bones, in particular medullary nails, of the type comprising an arched arm having a free distal end connectable to a proximal end of a nail head wherein said transverse holes are formed at a handle proximal portion, as well as a connection portion between the distal end and the proximal handle portion. The connection portion comprises at least one through-hole for receiving a guide tube for a drilling bit and locking means are associated to said at least one through-hole so as to lock in a stable position the corresponding tube inserted in the instrument.

Those locking means include a flexible second part of the handle that has a free end and is extended in a cantilever manner in parallel to the main part of the handle; when this second part is flexed by hand it interferes with the main part of the handle thus gripping the guide tube.

This gripping action is however not so stable and does not allow to free the surgeon hand for other handling necessities.

The technical problem forming the basis of the present invention is that of devising an improved instrument for the alignment of bone screws to be inserted in transverse nail holes for long bones, which has structural and functional characteristics such as to allow locking in position of the guide tubes inserted in the instrument handle while overcoming the drawbacks mentioned with reference to the prior art.

Another object of the invention is that of making it possible to achieve locking in position of the guide tubes by means of a simple manual movement, including that of a finger of a hand which is already employed gripping the instrument.

Another object of the invention is to devise an instrument of the aforementioned type which has a simple constructional design and is composed of a minimum number of component parts.

A further object of the invention is that of providing an instrument of the aforementioned type where the guide tube may also be removed with the same ease at the end of the operation.

SUMMARY OF THE INVENTION

The proposed solution forming the basis of the present invention is that of housing the tubes in through-holes formed in the central body of the instrument and equipping these holes with a manually operated quick-locking mechanism which allows the corresponding tube to be locked in position once its correct position has been defined.

Based on this proposed solution the technical problem is solved by an improved-structure instrument for allowing the alignment of fixing screws to be inserted in transverse holes of nails for long bones, in particular medullary nails, of the type comprising an arched arm having a free distal end connectable to a proximal end of a head of the nail in which said transverse holes are formed, and a proximal handle portion, as well as a connection portion between the distal end and the proximal handle portion, characterized in that said connection portion comprises at least one through-hole for receiving a guide tube for a drilling bit, said at least one through-hole having an axis coinciding with the axis of one of said transverse holes; manually operated quick-locking means being associated with said at least one through-hole so as to lock in a stable position the corresponding tube inserted in the instrument; wherein at least a chamber is formed inside the body of said connection portion around said through-hole for housing said locking means;

at least a lateral opening in communication with said chamber;

a two components quick-locking cam assembly forming said locking means: a first component being integral with said body of said connection portion around said guide tube and the other component including a cam and being angularly movable with respect to the first component;

a trigger element of said other component projecting from said lateral opening to be manually operated thus moving the first component with said cam interfering with said guide tube.

In mode details, the through-holes in the connection portion of the instrument are at least two in number and each of them has an axis coinciding with the axis of a corresponding transverse hole.

Moreover, the quick-locking means comprising a cam locking assembly housed in a chamber formed around a corresponding through-hole are provided for each of said through-holes.

The housing chamber has opposite openings that make it laterally accessible for said central body; the locking means which comprise a pair of components each provided with a corresponding through-hole for said tube are housed inside the chamber; one component being integral with the central body of the instrument and the other component being angularly movable with respect to the previous component so as to lock in position the tube by means of interference between the corresponding holes.

The corresponding holes of the two components are slightly axially offset with respect to each other. Moreover, one of said corresponding holes has a flat portion protruding along a chord of the circular shape of the hole in the manner of a cam.

The movable component is a butterfly member with a cylindrical body and a pair of opposite operating lugs integrally formed and laterally projecting from the central body of the instrument through said openings.

Moreover, at least one of the lugs is shaped with at least one concave surface which can be engaged by a finger of the hand of the orthopaedic surgeon so as to angularly rotate said butterfly member of the quick-locking assembly inside the respective housing chamber.

The cylindrical body is housed completely inside one of the chambers and is capable of rotating with limited angular travel until one of the two lugs comes into abutment against an edge of the openings.

Instead, the fixed component which cooperates with said butterfly member is essentially a sleeve inserted with limited play inside the cylindrical body and provided with a pin projecting perpendicularly from its inner wall for engaging with a guide slot formed in a bottom wall of said cylindrical body.

The characteristic features and advantages of the instrument according to the invention will emerge from the description, provided hereinbelow, of a non-limiting example of embodiment thereof with reference to the accompanying drawings.

BRIEF DESCRIPTION OF THE DRAWINGS

FIG. 4 shows a schematic cross-sectioned side view of the instrument according to FIG. 1;

FIGS. 5 and 6 show respective schematic front views of the detail of FIG. 3 in two different operating conditions;

DETAILED DESCRIPTION

Figure 1:
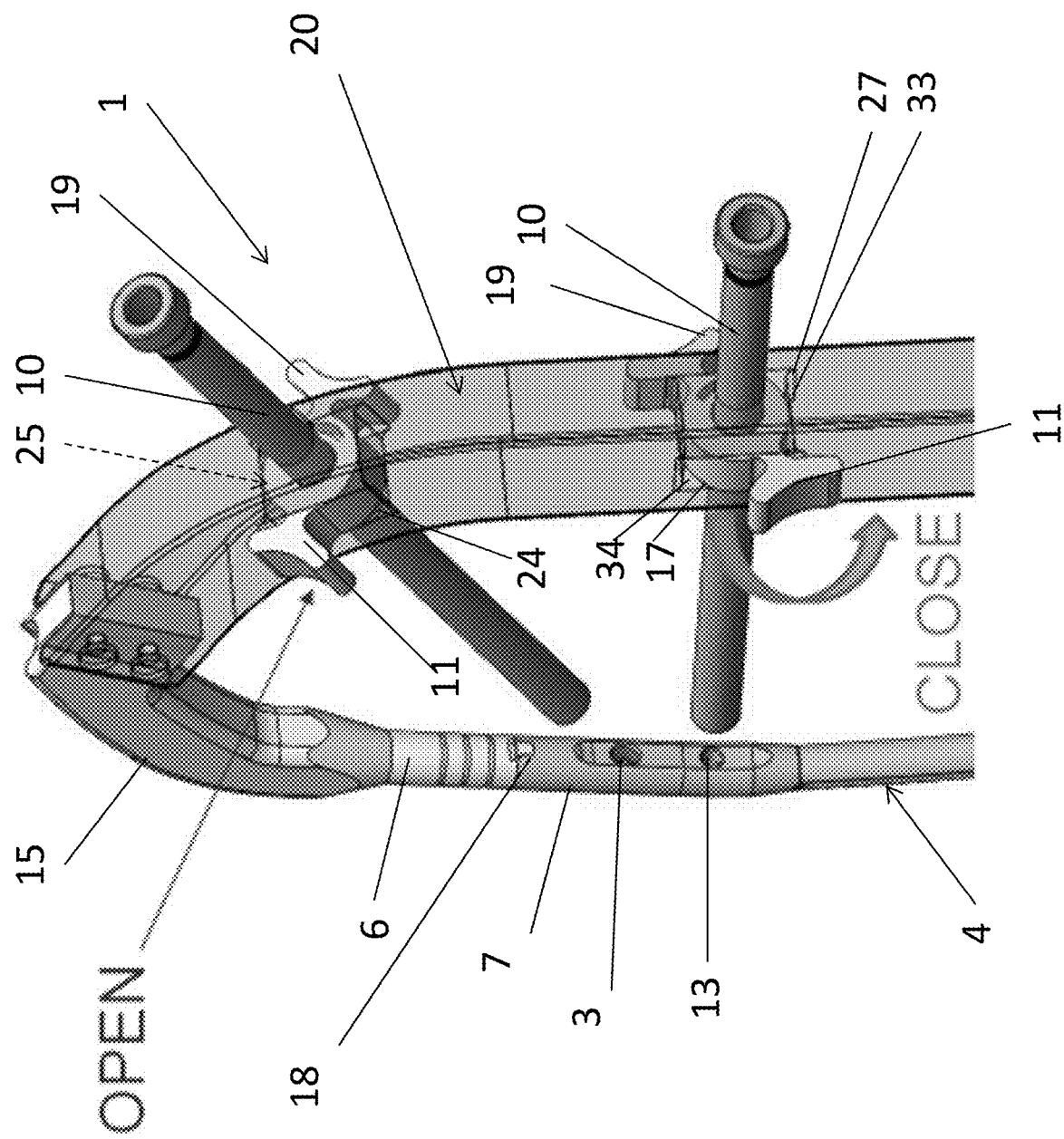
FIG. 1 shows a perspective and schematic view of the instrument provided according to the present invention for the alignment of fixing screws to be inserted in transverse holes of nails for long bones, in particular medullary nails.

With reference to these figures, 1 denotes overall and in schematic form an instrument designed according to the present invention with an improved structure for allowing the alignment of fixing screws 2 to be inserted into transverse holes 3 and 13 of a nail 4 for long bones, in particular a medullary nail.

Medullary nails are long nails intended to be inserted into the medullary cavity of long bones, such as the femur, the tibia or the humerus, in order to mend fractures which have occurred along at least a section of the long bone or in the trochanteric portion of a femur.

The nail 4 shown in the figures is intended, however, for use with paediatrics patients and/or adolescents and has dimensions compatible with this type of application. However, the principles of the present invention are applicable to any type of medullary nail without this resulting in any limitation of the rights of the Applicant.

More particularly, the nail 4 comprises a proximal head 7 and a stem 8 extending in the distal direction. The head 7 has an associated longitudinal axis of extension, while the stem 8 has a longitudinal axis inclined with respect to the axis of the head 7 of the nail.

The head 7 has, formed therein, at least two holes 3 and 13 transverse to its longitudinal axis.

The holes 3 and 13 are through-holes and are intended to receive fixing screws 2 (shown in FIG. 7) which reach the corresponding hole, penetrating through the cortex of the bone. The through-holes 3 and 13 are not necessarily perpendicular to the axis of the head 7, but may be inclined with respect to this axis and with respect to each other.

In order to form holes in the bone which may be directed towards and be aligned perfectly with the transverse holes 3, 13 of the head 7, drilling bits (not shown since conventional) are used and are guided by tubes 10 removably mounted on the instrument 1. The tubes 10 will be referred to below as pointers or guide tubes.

The instrument 1 according to the present invention has a general structure substantially in the form of an arched arm 15 with a distal end 6 which is free and can be connected to a proximal end 16 of the nail 4 and an opposite proximal handle portion 5.

The handle 5 is intended to be gripped by the orthopaedic surgeon in order to insert and position correctly the nail 4, which is connected at the distal end of the instrument, inside the medullary cavity of the bone involved in the operation.

The free distal end 6 of the instrument 1 is situated at one end of a slightly arched distal portion 15 provided with engaging means 18 for engaging and fastening the proximal end 16 of the head 7 of the nail 4 to the distal end 6 of the instrument 1.

Advantageously, according to the present invention, the instrument 1 comprises a connection portion 20 between said distal portion 15 and the handle 5. The connection portion 20 does not have substantially any interruption in continuity with the handle 5 and may be formed as one piece therewith. However, for the purposes of the present invention, the connection portion 20 is to be regarded as separate from the handle and could also be mounted removably on the said handle 5.

This connection portion 20 forms the central body of the instrument 1 and is the portion which has, formed therein, through-holes 23 and 33 intended to receive the guide tubes 10 for the drilling bits. In one embodiment it is possible to envisage also a single hole in the connection portion 20 of the instrument.

Figure 2:
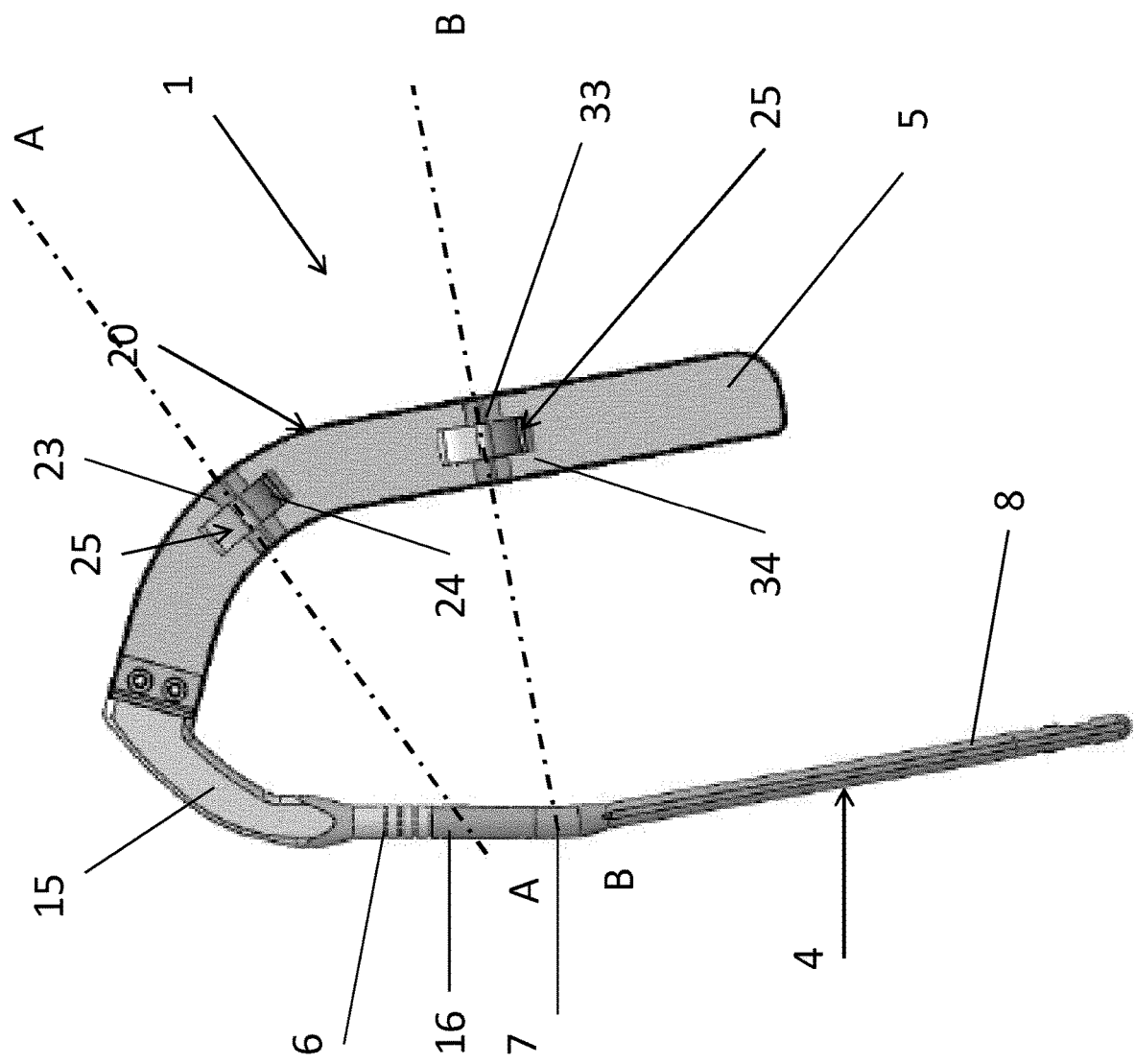
FIG. 2 shows a schematic, vertical, side-elevation view of the instrument according to the invention.

Each of the holes 23 and 33 has a respective axis A-A and B-B, clearly visible in FIG. 2, which is aligned and coincides with the axis of a respective transverse hole 3 and 13 in the head 7 of the nail 4.

Essentially, the axes A-A and B-B are coaxial with the axes of the transverse holes 3, 13 in the nail 4 so as to guide the bone drilling bits until they reach the transverse holes 3 and 13.

Still according to the present invention, the tubes 10 are supported in the central body 20 of the instrument 1 by means of the through-holes 23 and 33.

More particularly, locking means 25 are provided for stably locking the tubes 10 in position inside the respective through-holes 23 and 33.

Inside the body 20, in the central position of each through-hole 23 and 33, a respective chamber 24, 34 for housing the locking means 25 is provided. Each chamber 24, 34 is substantially a square seat having opposite openings 17 and 27 which make it laterally accessible for the central body 20. The aforementioned locking means 25 are provided inside each of these chambers.

Each chamber 24 or 34 houses inside it with limited axial play the aforementioned locking means 25 which comprise a quick-locking cam assembly formed by means of two components: one component 39 integral with the central body 20 of the instrument and one component 9 angularly movable with respect to the component integral with the body 20.

More particularly, the quick-locking assembly is manually operated and comprises a trigger comprising a first butterfly member 9 with a main cylindrical body 29 and a second coupling member 39 inserted inside the cylindrical body 29. The coupling member 39 is rigidly connected to the central body 20 of the instrument 1.

The butterfly member 9 of the trigger component has a pair of opposite wings 11, 19 or operating lugs formed integrally with the cylindrical body 29 and laterally projecting from the central body 20 of the instrument 1 through the openings 17 and 27.

Each of the lugs 11, 19 is shaped with at least one concave surface 28 which can be engaged by a finger of the hand of the orthopaedic surgeon so as to manually operate the locking means 25, angularly displacing the butterfly member 9 of the quick-locking assembly inside the respective housing chamber 24, 34.

The cylindrical body 29 is housed entirely inside one of the chambers 24, 34 and is able to rotate with limited angular travel until one of the two lugs 11 or 19 comes into abutment against an edge of the openings 17 or 27, when no tube is inserted.

The cylindrical body 29 has a bottom wall 26 provided with a hole 22 through which the tube 10 passes when the butterfly member is housed inside the respective chamber 24, 34.

The hole 22 has a flat portion 21 protruding essentially along a chord of the circular shape of the hole 22 so as to form a cam.

The diameter of the hole 22 is slightly greater than the outer diameter of the tube 10.

A curved slot 36 is also provided in the bottom wall 26 of the cylindrical body 29 in a predefined spaced relationship with respect to the hole 22 and concentric with it along a short section.

Figure 3:
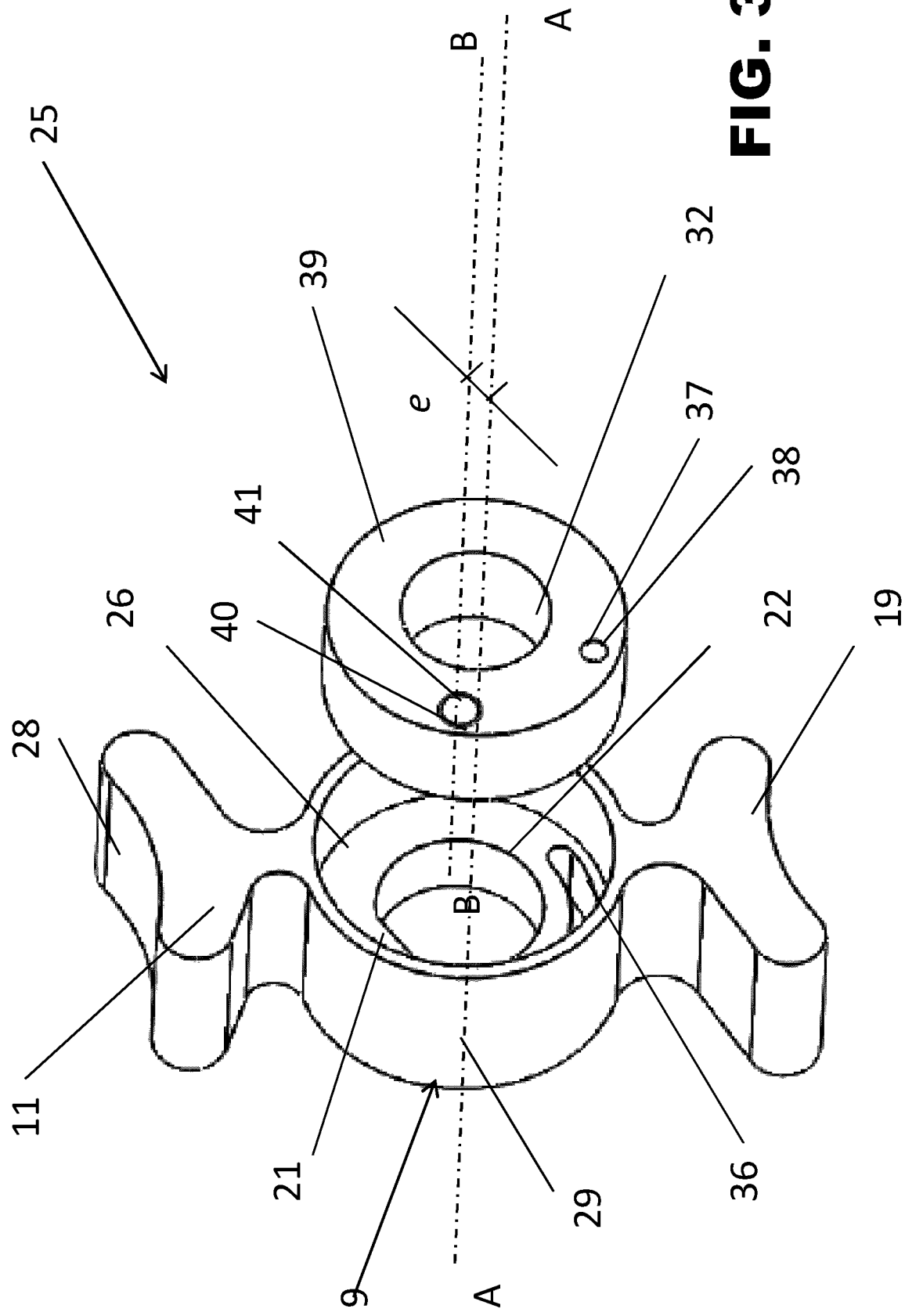
FIG. 3 shows a perspective and schematic view of a detail of the instrument according to the invention.

The coupling member 39 which cooperates with the butterfly member 9 is essentially a sleeve inserted with limited play inside the cylindrical body 29 and provided centrally with a hole 32, Advantageously, the hole 32 is slightly axially offset with respect to the hole 22 of the cylindrical body 29. The eccentricity e between the axis A-A of the hole 22 and the axis B-B of the hole 32 is shown schematically in FIG. 3 and consists of a few millimetres.

The diameter of the hole 32 corresponds substantially to the outer diameter of the tube 10.

A pin 37 projects perpendicularly from the inner wall of the sleeve 39 so as to be inserted inside the slot 36 and be guided inside this slot 36 along a predefined angular travel path equal to the extension of the said slot. The pin 37 passes through a hole 38 formed in turn inside the sleeve 39.

The sleeve 39 also has a hole 40 for the insertion of a presser 41 which performs the function of a friction shoe and which allows the sleeve 39 to be fastened to the housing chamber 24 or 34 so that the sleeve 39 is rigidly connected together with the central body 20 of the instrument 1.

More particularly, the hole 40 is threaded and is intended for insertion of the presser 41 which has the function of eliminating undesirable movements of the butterfly member 9 when the mechanism is not closed so as to lock a tube in position. In this way it is avoided that the user has to deal with freely rotating components when the instrument is being assembled and prepared and when the butterfly member 9 of the trigger is still in the "open" position.

At the same time, the pin 37 which rigidly fixes the member 39 to the body 9 passes inside the hole 38 of the sleeve 39 and therefore inside the slot 36 of the butterfly member 9.

Essentially, only the butterfly member 9, with the lugs 11, 19 projecting from the openings 17 and 27, is rotationally movable with friction and with limited angular travel inside the associated housing chamber 24 or 34 formed in the central body of the instrument 1.

This butterfly member 9 of the quick-locking cam assembly cooperates with the sleeve-like coupling member 39 so as to allow quick locking in position of the corresponding guide tube.

As can be clearly seen in FIGS. 5 and 6, in the open position the two holes 32 and 22 of the respective components 39 and 29 of the cam locking assembly are substantially axially offset as a result of the eccentricity e, and thus a relative rotation of the components 39 and 20 causes a constriction of the guide tube 10 inserted inside the holes 22 and 32 by means of the flat cam portion 21 and stable locking in position of the said tube.

In other words, the guide tube 10 may be inserted without difficulty inside one of the housing holes 23 or 33 provided in the central connection body 20 of the instrument via the holes 22 and 32 of the locking assembly.

Once the tube 10 is correctly seated, the orthopaedic surgeon may decide to lock the tube 10 easily and rapidly in the closing position once it has been ensured that the same has its end situated next to the skin, and then the bone, of the patient so as to allow a tissue-protection function to be performed during incision and drilling of the bone until one of the transverse holes 3 or 13 of the head 7 of the nail already inserted inside the medullary cavity of the bone is reached.

By means of a simple manual action on one or other of the lugs 11, 19 the surgeon is able to displace angularly the butterfly member 9 of the quick-locking cam assembly and position it in the configuration shown in FIG. 6 where the flat portion 21 of the hole 22 interferes with the diameter of the hole 32 and locks the tube 10 by means of interference in the desired position.

In this connection particular attention is drawn to the relative displacement of the guide slot 36 with respect to the pin 37 of the coupling member integral with the instrument 1.

Once the hole has been formed in the bone owing to guiding of a drilling bit by means of the tube 10, a fixing screw 2 must be introduced so as to engage with one of the transverse holes 3 or 13 in the head 7 of the nail 4.

Figure 7:
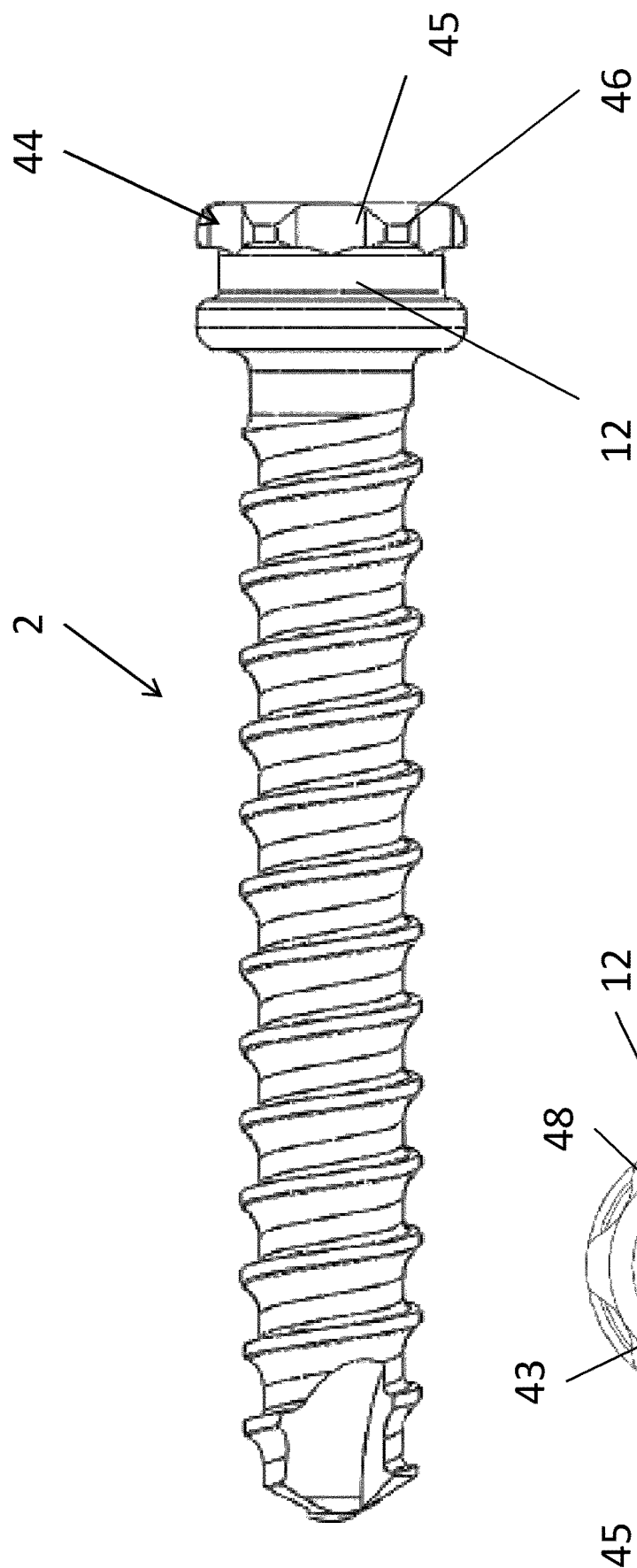
FIG. 7 shows a side view of a fixing screw intended to be inserted in a transverse hole of a medullary nail.
Figure 8:
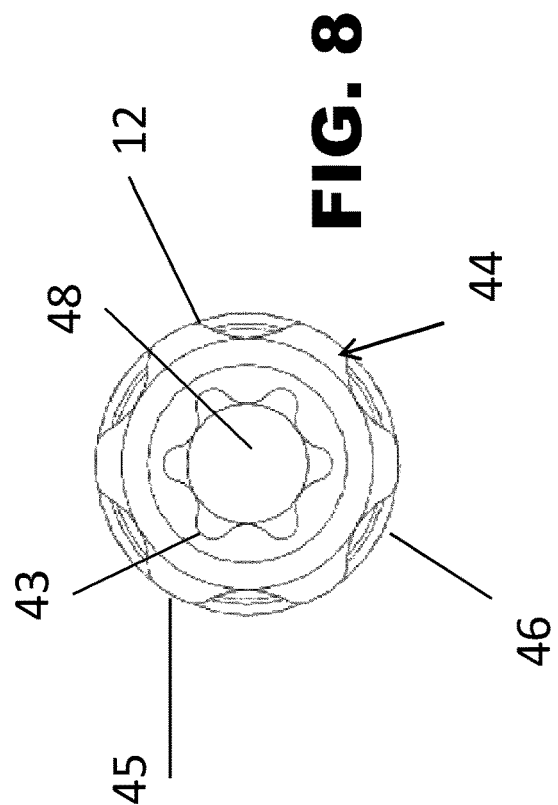
FIG. 8 shows a view from above of the head of the screw according to FIG. 7.
Figure 9:
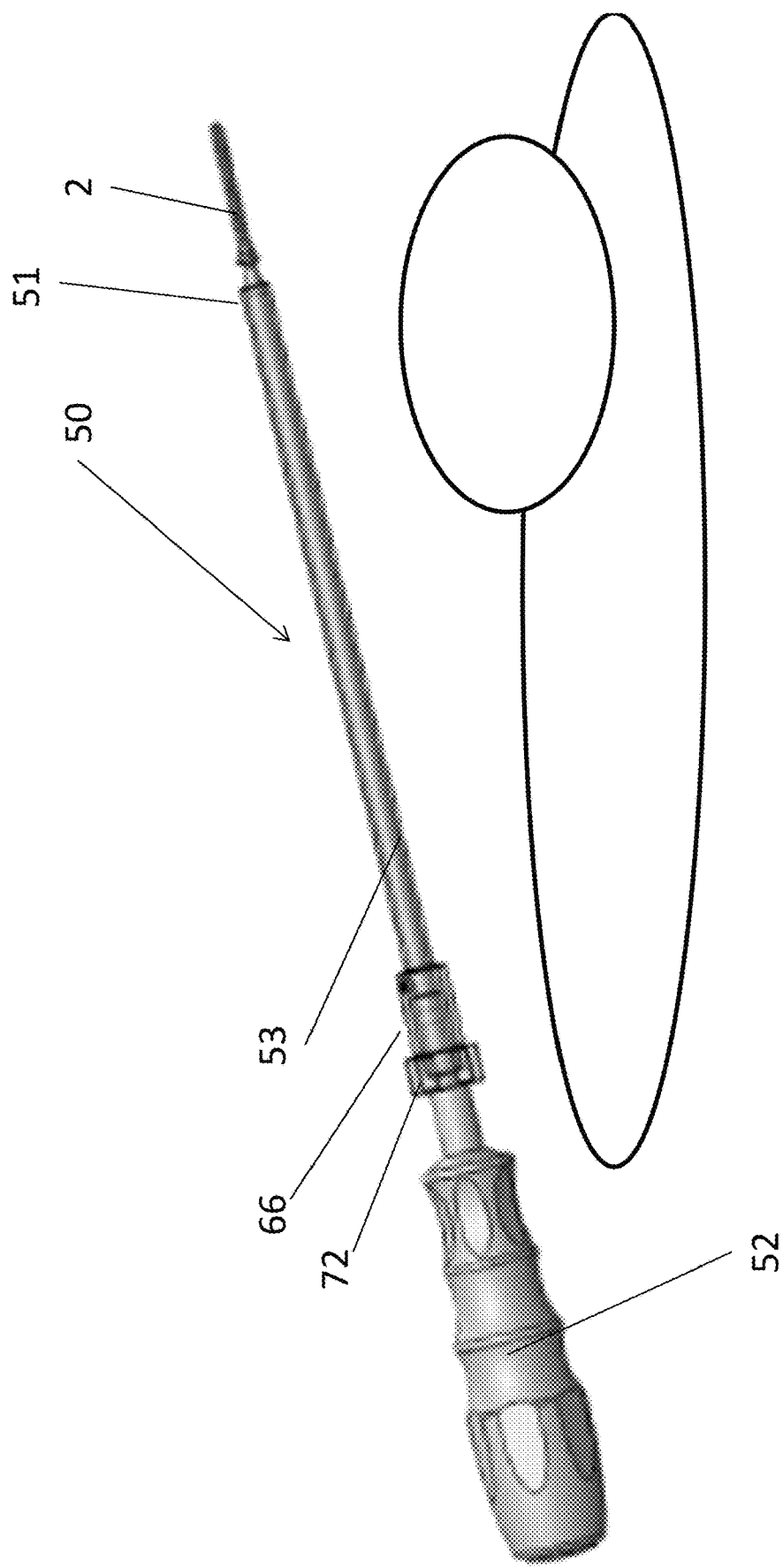
FIG. 9 shows a perspective yew of a tool used with the instrument according to the present invention for installation of the screws according to FIG. 7.

In order to grip, insert and engage in a distal position a screw 2 inside the corresponding hole 3, 13 of the nail 4, it is envisaged using, according to the present invention, a tool 50 shown in FIG. 7.

This tool 50 may be equipped with a screwdriver having an operative distal end 51 and a proximal handle end 52.

The tool 50 extends along its longitudinal axis and may comprise a shank 53 removably engaged with the handle 52. Obviously it is quite possible for the shank to be fastened beforehand to the handle without this limiting in any way the rights of the Applicant. The screw 2 which is inserted inside the transverse holes of the head 7 of the nail 4 has a head 12 shaped to allow a form-fit with the distal end 51 of the tool 50.

For this purpose the head 12 has a peripheral crown 44 formed by an alternation of protuberances 45 and recesses 46 which are regularly spaced relative to each other.

The head 12 has centrally a recess 48 which is in turn shaped in the manner of a plurality of lobes 43 which correspond, in terms of number and position, to the lobes and the protuberances 45 of the recess in the screw.

In the preferred example of embodiment described here by way of a non-limiting example, the crown 44 has an alternating arrangement of six protuberances and six recesses, but it is quite possible to provide a different number and arrangement thereof. This corresponds to a central recess 48 with a hexalobular form.

Advantageously, the distal end 51 of the tool 50 is configured so as to be able to engage with the head 12 of the screw 2 both on the outside thereof and on the inside thereof in the central recess 48.

Figure 10:
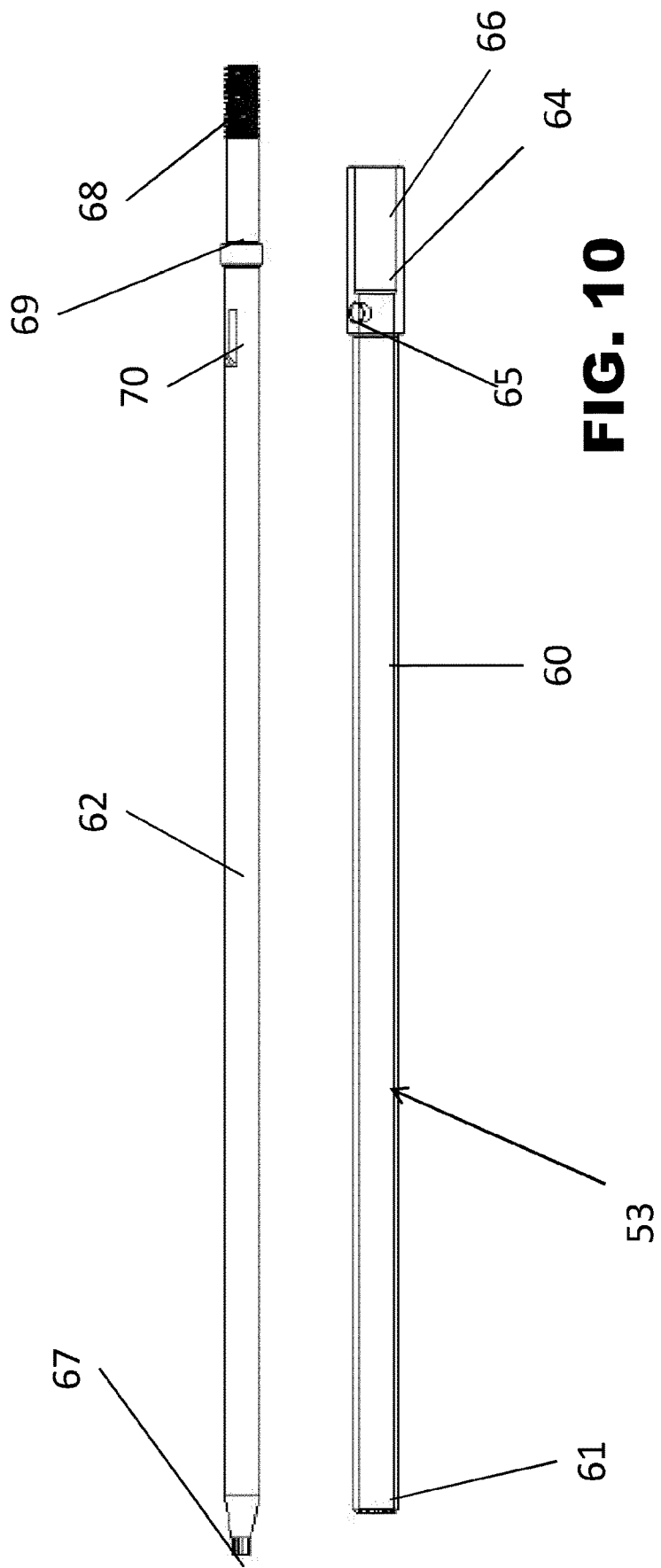
FIG. 10 shows a side view of a pair of components of the tool according to FIG. 9.
Figure 12:
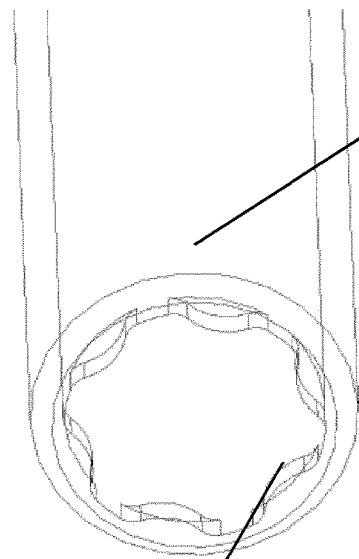
FIG. 12 shows a schematic view of a detail of the end of the tool according to FIG. 9.
Figure 11:
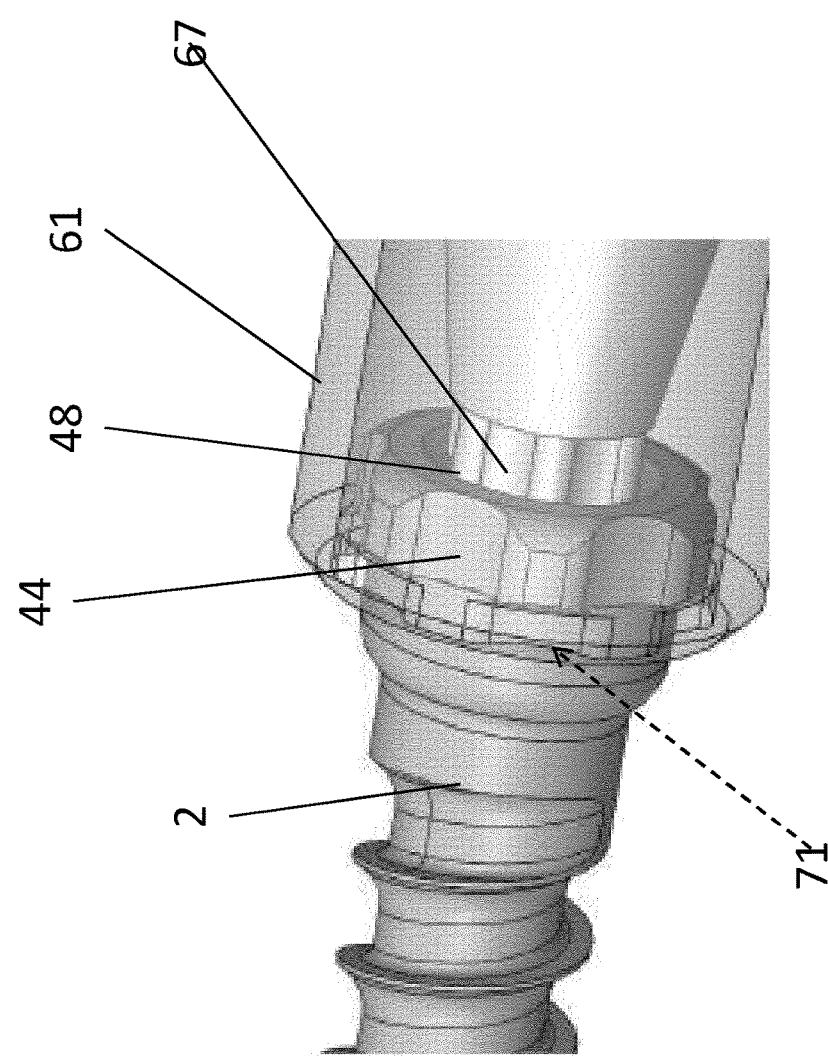
FIG. 11 shows a perspective view of a detail of the tool according to FIG. 9 at the moment where it engages with the head of the screw according to FIG. 7.

As shown in FIG. 10, the shank 53 of the tool 50 comprises two main components, an outer component 60 and an inner component 62. A third tubular component 66 rigidly connected to a proximal ring 72 cooperates with the outer component 60 so as to rotate it manually with respect to the inner component 62.

The outer component 60 is a tubular rod with distal end 61 intended to surround the crown 44 of the head 12 of the screw 2 and engage with it by means of a matching form 71. The proximal end 64 of the tubular rod 60 is connected to the third component which is a proximal tubular element 66 with a larger diameter, provided with a pin 65 or a presser projecting inwards. The tubular element is rigidly connected to the proximal ring 72.

The inner component 62 is a core with a distal end 67 which is tapered and has a cross-section shaped with the same form as the central recess 48 of the screw 2. The proximal end 68 of the core 62 is threaded so as to be able to be screwed onto the handle 52 of the tool 50.

At a predefined distance from this threaded proximal end 68 there is an annular stop element 69 intended to form an end-of-travel stop for the axial sliding movement of the tubular element 66 when the core 62 is inserted concealingly inside the tubular rod 60.

A spring is optionally provided, being inserted between the annular stop element 69 and the threaded proximal end 68 so as to keep the instrument in position when it is in the closed and open positions.

The core 62 is also provided with a slit 70 extending along a short longitudinal section in a distal position with respect to the annular stop element 69 and intended to receive the pin 65 or a presser formed on the tubular element 66 so as to form an axial sliding guide for this pin 65.

When the core 62 is mounted coaxially inside the tubular rod 60 of the tool 50 a small relative axial movement of the two components 60 and 62 is possible, this allowing the respective distal ends 61 and 67 to be radially aligned and to engage with a form-fit with the head 12 of the screw 2.

In fact, the inner form of the distal end 61 of the tubular rod 60 engages with the perimetral crown 44 of the screw 2, while the shaped distal end 67 of the core 62 engages by means of a form-fit with the central recess 48 of the same screw 2.

Essentially, it is as though the tool 50 had a distal end 51 comprising an outer component 61 intended for a form-fit with the head 12 of said screw 2 and an inner component 62 intended for a simultaneous form-fit with the central recess 48 of said screw 2.

Moreover, the aforementioned outer distal end 61 and inner distal end 67 are axially slidable relative to each other following the sliding movement of the core 62 inside the tubular rod 60 on the guide of the pin 65 inside the slit 70.

In this way, the retention of the screw 2 at the distal end 51 of the tool 50 is ensured by a double form-fit.

Moreover, the inner form-fit, namely that of the distal end 67 of the core 62 also allows the screw 2 to be rotationally operated, being substantially a form-fit which also allows a twisting moment to be transferred.

In this way, not only is stable gripping of the screw 2 ensured at the distal end 51 of the tool 50, but it is also possible to screw or unscrew the screw into/from the corresponding seat formed by the transverse hole in the head 7 of the nail 4 without adversely affecting in any way the aseptic condition of the components used.

From the above description it is clear that the instrument 1 and the associated tool 50 according to the present invention may be used in combination as parts of a single operating kit.

The tool 50 offers the great advantage that it has a simple and low-cost constructional design, ensuring stable retention of the heads of the bone screws during the delicate phase when they are inserted into transverse through-holes of the medullary cavity and also easy removal thereof during explantation.

The invention claimed is:

1. An improved-structure instrument for allowing the alignment of fixing screws to be inserted in transverse holes of nails for long bones, in particular medullary nails, of the type comprising:
    an arched arm having a free distal end connectable to a proximal end of a head of the nail in which said transverse holes are formed, and
    a proximal handle portion as well as a connection portion between the free distal end and the proximal handle portion,
    at least one through-hole in said connection portion for receiving a guide tube for a drilling bit, said at least one through-hole having an axis coinciding with the axis of one of said transverse holes;
    locking means associated with said at least one through-hole so as to lock in a stable position the corresponding tube inserted in the instrument; wherein
    at least a chamber is formed inside a body of said connection portion around said through-hole for housing said locking means;
    at least a lateral opening in communication with said chamber;
    a quick-locking cam assembly, including a first component and another component, forming said locking means: the first component of the quick-locking cam assembly being integral with the body of the connection portion and placed around said guide tube, and the other component of the quick-locking cam assembly including a cam and being angularly movable with respect to the first component; said other component being provided with a first hole through which the tube passes; said first component being provided with a second hole through which the tube passes; the first and second holes are slightly axially offset; said first hole having a flat portion protruding essentially along a chord of the circular shape of the first hole so as to form the cam of the other component of the quick-locking cam assembly;
    a trigger element of said other component projecting from said lateral opening to be manually operated thus moving the other component with said cam interfering with said guide tube, a relative rotation of the components causes a constriction of the guide tube inserted into the holes by means of the flat portion and stable locking in position of the said guide tube,
    wherein the at least one chamber has opposite openings that make it laterally accessible for said body of the connection portion; said locking means being housed in the chamber and comprising the quick-locking cam assembly including the first component and the other component, each component being provided with a corresponding through-hole for said tube; one component being integral with the body of the connection portion and the other component being angularly movable with respect to the first component so as to lock in position the tube by means of interference between the corresponding holes,
    wherein the other component of the quick-locking cam assembly is a butterfly member with a cylindrical body and a pair of opposite operating lugs integrally formed and laterally projecting from the body of the connection portion through said lateral openings, and
    wherein at least one of the lugs is shaped with at least one concave surface which can be engaged by a finger of a hand of the orthopaedic surgeon so as to angularly rotate said butterfly member of the quick-locking assembly inside the respective housing chamber.

2. The instrument according to claim 1, wherein said through-holes in the connection portion of the instrument are at least two in number and each of them has an axis coinciding with the axis of a corresponding transverse hole.

3. The instrument according to claim 2, wherein locking means comprising the quick-locking cam assembly housed in a respective chamber formed around corresponding through-holes in the connection portion are provided for each of said through-holes in the connection portion.

4. The instrument according to claim 3, wherein said cylindrical body is housed completely within one of the chambers and is capable of rotating with limited angular travel until one of the two lugs comes into abutment against an edge of the openings in the absence of the guide tube.

5. The instrument according to claim 1, wherein the fixed component which cooperates with said butterfly member is essentially a sleeve inserted with play inside the cylindrical body and provided with a pin perpendicularly projecting from its inner wall for engaging with a guide slot formed in a bottom wall of said cylindrical body.

6. The instrument according to claim 1, including fixing screws to be inserted in transverse holes of nails wherein at least one of said fixing screws comprises a head shaped as a crown with a central recess for a form-fit with the distal end of a tool for retaining the screw.

7. The instrument according to claim 6, wherein said head shaped as a crown has an alternation of regularly spaced protuberances and recesses.

8. The instrument according to claim 6, wherein said central recess is shaped in the manner of a plurality of lobes which correspond to said protuberances in terms of number and positioning.

9. The instrument according to claim 6, wherein it comprises a tool having at least one distal end comprising an outermost end intended for a form-fit with the head of said screw and an inner end intended for a simultaneous form-fit with the central recess of said screw.

10. The instrument according to claim 9, wherein said outer end and inner end are axially slidable relative to each other.

\* \* \* \* \*